United States Patent
Okamoto et al.

(10) Patent No.: US 8,182,827 B2
(45) Date of Patent: May 22, 2012

(54) OIL-IN-WATER EMULSION COMPOSITION

(75) Inventors: Tohru Okamoto, Yokohama (JP); Haruhiko Inoue, Yokohama (JP); Hideo Nakajima, Yokohama (JP)

(73) Assignee: Shiseido Co., Ltd., Tokyo (JP)

( * ) Notice: Subject to any disclaimer, the term of this patent is extended or adjusted under 35 U.S.C. 154(b) by 258 days.

(21) Appl. No.: 12/249,657

(22) Filed: Oct. 10, 2008

(65) Prior Publication Data

US 2009/0041811 A1    Feb. 12, 2009

Related U.S. Application Data

(63) Continuation of application No. 10/682,873, filed on Oct. 14, 2003, now abandoned.

(51) Int. Cl.
*A61K 8/02* (2006.01)

(52) U.S. Cl. ......................... 424/401; 514/844
(58) Field of Classification Search .................. 424/401; 514/844
See application file for complete search history.

(56) References Cited

U.S. PATENT DOCUMENTS 4,767,625 A * 8/1988 Mitsuno et al. ............... 424/401
5,693,255 A * 12/1997 Okamoto et al. ............... 516/58

* cited by examiner

*Primary Examiner* — Gina C Yu
(74) *Attorney, Agent, or Firm* — Townsend & Banta

(57) ABSTRACT

The present invention is an oil-in-water emulsion composition containing a hydrophilic non-ionic surfactant or hydrophilic anionic surfactant, a higher aliphatic alcohol, water, and an oil ingredient which meets specific conditions. This is an oil-in-water emulsion composition with good high temperature stability and usability, and can be used as a cream-like endermic liniment such as a cosmetic.

11 Claims, No Drawings

OIL-IN-WATER EMULSION COMPOSITION

FIELD OF THE INVENTION

This invention relates in general to an oil-in-water emulsion composition, and more particularly to an oil-in-water emulsion composition which has superior stability over time and offers good usability.

BACKGROUND OF THE INVENTION

Generally, an oil-in-water cream preparation emulsified with a non-ionic surfactant is prepared by forming an α-gel in which the molar ratio of the non-ionic surfactant and the higher aliphatic alcohol is 1:3 in the system to solidify the cream.

Therefore, in order to stabilize this preparation, a sufficient amount of the α-gel needs to be formed to solidify the cream and prevent creaming; usually, 4 wt % or more of a amphiphilic substance such as a higher aliphatic alcohol and a non-ionic surfactant are blended in the α-gel.

However, when the oil-in-water cream is prepared with the aforementioned method, while the cream is stabilized by the α-gel, which is needed to solidify the cream, its presence gives a heavy sensation at the time of application, making it very difficult to obtain a cream with a refreshing and light sensation during use.

When the blend ratio of the surfactant is reduced for the purpose of improving the sensation during use, the hardness of the system decreases and there is a problem in that it fails to become cream or creaming occurs at high temperatures.

Based on the aforementioned situation, the inventors conducted earnest research to solve said problem and discovered that an oil-in-water emulsion composition with superior stability over time and usability can be obtained by blending in a hydrophilic non-ionic surfactant or hydrophilic anionic surfactant and a higher aliphatic alcohol under specific conditions in the oil-in-water emulsion composition, thus completing the present invention.

The object of the present invention is to provide an oil-in-water emulsion composition which has superior stability over time and offers satisfactory sensations during use.

DISCLOSURE OF THE INVENTION

That is, the present invention provides an oil-in-water emulsion composition containing a hydrophilic non-ionic surfactant or hydrophilic anionic surfactant, a higher aliphatic alcohol, water, and an oil ingredient(s) which meets the following conditions (1)-(4):

(1) The hydrophilic non-ionic surfactant, the higher aliphatic alcohol, and water form a gel, and the gel thus formed has a transition temperature of 60° C. or higher.

(2) The blend ratio of the hydrophilic non-ionic surfactant which forms said gel is 0.1 wt % or more and less than 0.5 wt % of the total amount of the oil-in-water emulsion composition.

(3) The molar blend ratio of the hydrophilic non-ionic surfactant and the higher aliphatic alcohol which form the aforementioned gel is 1:3.

(4) An extra higher aliphatic alcohol or amphiphilic substance which is not involved in the formation of the gel is contained, and its blend ratio is 0.5-10 wt %.

Also, the present invention provides said oil-in-water emulsion composition wherein said oil-in-water emulsion composition is a cream-like endermic liniment.

THE BEST MODES OF THE EMBODIMENTS

The configuration of the present invention is described in detail below.

1: The Invention of Claims 1 and 2

For the hydrophilic non-ionic surfactant used in the present invention, an alkyl ether type surfactant or an alkyl ester type surfactant with a linear chain alkyl group having 16 or more carbon atoms is preferable; examples include POE alkyl ethers such as POE stearyl ether and POE behenyl ether and POE alkyl esters such as polyethylene glycol monostearate. More preferable are surfactants with a HLB of 12-20; examples include POE alkyl ethers such as POE oleyl ether, POE stearyl ether, and POE behenyl ether.

Examples of the higher aliphatic alcohol used in the present invention include lauryl alcohol, cetyl alcohol, stearyl alcohol, behenyl alcohol, myristyl alcohol, oleyl alcohol, cetostearyl alcohol. One, two or more of these are blended in. Preferable is a mixture of two or more higher aliphatic alcohols. More preferable is a combination for which the melting point of the mixture is 60° C. or higher. If this melting point is lower than 60° C., then the temperature stability of the system decreases and creaming may occur, depending on the formula. For example, a combination of stearyl alcohol and behenyl alcohol is preferably used.

The oil-in-water emulsion composition of the present invention requires that the gel formed by the aforementioned higher aliphatic alcohol, the hydrophilic non-ionic surfactant, and water have a transition temperature of 60° C. or higher; preferably 65° C. or higher. If the transition temperature of this gel is lower than 60° C., then the temperature stability of the system decreases and creaming may occur. This gel is usually an α-gel. An α-gel is a gel prepared by adding water to a complex composed of a higher aliphatic alcohol and a hydrophilic non-ionic surfactant which assumes the α structure ("Physical Chemistry of Cetyl Alcohol", Shoji Fukushima, Fragrance Journal Co., Ltd.).

The blend ratio of the hydrophilic non-ionic surfactant which forms the aforementioned gel needs to be 0.2-1.0 wt %, preferably 0.3-0.8 wt %, of the total amount of the oil-in-water emulsion composition. If the blend ratio is less than 0.2 wt % then the temperature stability of the system decreases and creaming may occur. If it is over 1.0 wt % then the sensation during application becomes heavy and a product with satisfactory usability cannot be obtained.

In the aforementioned gel, the blend ratio of the hydrophilic non-ionic surfactant and the higher aliphatic alcohol which form the gel is 1:3 (molar ratio). In the present invention, "gel" refers to a complex composed of the lamella structure of the hydrophilic non-ionic surfactant and the higher alcohol formed in the water phase. The formation of a complex by the hydrophilic non-ionic surfactant and the higher alcohol can be verified with a DSC (differential scanning calorimeter). The heat absorption curve of the sample prepared by mixing these two and dispersing them in water shows a single heat absorption peak which is at a higher temperature than the absorption peaks obtained by dissolving or dispersing either of them separately in water; when the blend ratio of the higher alcohol is low, (due to a shortage of the higher alcohol) the temperature of the heat absorption peak of the complex is low. This temperature rises as the blend ratio of the higher alcohol increases. When, after completion of the complex structure, the higher alcohol becomes in excess, this temperature plateaus and a peak due to the excess higher alcohol appears. It is known that, when a hydrophilic non-ionic surfactant with a single alkyl chain and a higher alcohol with a single alkyl chain form a complex, the blend ratio at which the complex structure is completed is one mole of the hydrophilic non-ionic surfactant to three moles of the higher alcohol.

In the present invention, an extra amount of the higher aliphatic alcohol or an amphiphilic substance which is not involved in the formation of the aforementioned gel is contained and its blend ratio is 1-10 wt % of the total amount of the oil-in-water emulsion composition.

The description of the higher aliphatic alcohol in this case is the same as that of the higher aliphatic alcohol which is involved in the formation of the aforementioned α-gel. Usually, the same higher aliphatic alcohol is added in excess. That is, since the molar composition ratio of the hydrophilic non-ionic surfactant and the higher aliphatic alcohol that form the gel is 1:3, the blend ratio value of the higher aliphatic alcohol which is involved in the α-gel is three times the amount (in moles) of the hydrophilic non-ionic surfactant multiplied by the average molecular weight of the higher aliphatic alcohol. Therefore, the blend ratio of the higher aliphatic alcohol must be higher than this value and the excess amount must be 1-10 wt %. An amphiphilic substance other than a higher aliphatic alcohol can also be blended in. The melting point of the amphiphilic substance is preferably 55° C. or higher, more preferably 60° C. or higher. If this melting point is lower than 55° C. then the temperature stability of the system decreases and creaming may occur. Examples of preferable amphiphilic substances include glyceryl monoalkyl ether, monoglyceride, and batyl alcohol. When both the higher aliphatic alcohol and the amphiphilic substance which are not involved in the formation of the gel are blended in, the total blend ratio of the two is 1-1.0 wt %.

As mentioned above, the blend ratio of the extra amount of the higher aliphatic alcohol or the amphiphilic substance other than a higher alcohol which is not involved in the formation of the gel needs to be 1.0-10 wt % of the total amount of the oil-in-water emulsion composition. If this blend ratio is less than 1.0 wt %, then the amount of the crystals of the extra higher alcohol or the amphiphilic substance is small and maintaining sufficient high temperature stability may not be possible. If the blend ratio is more than 10 wt % then the hardness becomes too high, depending on the composition, and the sensation during use becomes poor. Both can be blended in together, and the total blend ratio should be 1-10 wt %.

In the present invention, in addition to the aforementioned hydrophilic non-ionic surfactant, which is an essential ingredient to form the gel, lipophilic non-ionic surfactants, cationic surfactants, anionic surfactants or amphiphilic surfactants can be blended in within the range that would not affect the effects of the present invention. A hydrophilic non-ionic surfactant which is not involved in the formation of the gel can also be present.

The blend ratio of water in the oil-in-water emulsion composition of the present invention, which is determined according to the product, is in the range of 40-90 wt % of the total amount of the oil-in-water emulsion composition.

Selection of the oil ingredient depends on the product; the blend ratio is 5-50 wt % of the total amount of the oil-in-water emulsion composition. In the present invention, the oil ingredient does not include the aforementioned higher aliphatic alcohol and the amphiphilic substance which are the essential ingredients.

2: The Invention of Claims 3 and 4

For the hydrophilic anionic surfactant used in the present invention, N-acyl-L-glutamic acid salt or monoalkylphosphoric acid salt with a linear chain alkyl group having 16 or more carbon atoms is preferable; examples include monosodium N-stearoylglutamate, monosodium N-palmitoylglutamate, triethanolamine N-stearoylglutamate, and sodium cetylphosphate.

Examples of the higher aliphatic alcohol used in the present invention include lauryl alcohol, cetyl alcohol, stearyl alcohol, behenyl alcohol, myristyl alcohol, oleyl alcohol, cetostearyl alcohol, etc. One, two or more of these are blended in. Preferable is a mixture of two or more higher aliphatic alcohols. More preferable is a combination for which the melting point of the mixture is 60° C. or higher. If this melting point is lower than 60° C., then the temperature stability of the system decreases and creaming may occur, depending on the formula. For example, a combination of stearyl alcohol and behenyl alcohol is preferably used.

The oil-in-water emulsion composition of the present invention requires that the gel formed by the aforementioned higher aliphatic alcohol, the hydrophilic anionic surfactant, and water have a transition temperature of 60° C. or higher; preferably 65° C. or higher. If the transition temperature of this gel is lower than 60° C. then the temperature stability of the system decreases and creaming may occur. This gel is usually an α-gel. An α-gel is a gel prepared by adding water to a complex composed of a higher aliphatic alcohol and a hydrophilic surfactant which assumes the α structure ("Physical Chemistry of Cetyl Alcohol", Shoji Fukushima, Fragrance Journal Co., Ltd.).

The blend ratio of the hydrophilic anionic surfactant which forms the aforementioned gel needs to be 0.1 wt % or more and less than 0.5 wt % of the total amount of the oil-in-water emulsion composition. If the blend ratio is less than 0.1 wt % then the temperature stability of the system decreases and creaming may occur. If it is over 0.5 wt % then the sensation during application becomes heavy and a product with satisfactory usability cannot be obtained.

In the aforementioned gel, the blend ratio of the hydrophilic anionic surfactant and the higher aliphatic alcohol which form the gel is 1:3 (molar ratio). In the present invention, "gel" refers to a complex composed of the lamella structure of the hydrophilic anionic surfactant and the higher alcohol formed in the water phase. The formation of a complex by the hydrophilic anionic surfactant and the higher alcohol can be verified with a DSC (differential scanning calorimeter). The heat absorption curve of the sample prepared by mixing these two and dispersing them in water shows a single heat absorption peak which is at a higher temperature than the absorption peaks obtained by dissolving or dispersing either of them separately in water; when the blend ratio of the higher alcohol is low, (due to a shortage of the higher alcohol) the temperature of the heat absorption peak of the complex is low. This temperature rises as the blend ratio of the higher alcohol increases. When, after completion of the complex structure, the higher alcohol becomes in excess, this temperature plateaus and a peak due to the excess higher alcohol appears. It is known that, when a hydrophilic anionic surfactant with a single alkyl chain and a higher alcohol with a single alkyl chain form a complex, the blend ratio at which the complex structure is completed is one mole of the hydrophilic anionic surfactant to three moles of the higher alcohol.

In the present invention, an extra amount of the higher aliphatic alcohol or an amphiphilic substance which is not involved in the formation of the aforementioned gel is contained and its blend ratio is 0.5-10 wt % of the total amount of the oil-in-water emulsion composition.

The description of the higher aliphatic alcohol in this case is the same as that of the higher aliphatic alcohol which is involved in the formation of the aforementioned α-gel. Usually, the same higher aliphatic alcohol is added in excess. That is, since the molar composition ratio of the hydrophilic anionic surfactant and the higher aliphatic alcohol that form the gel is 1:3, the blend ratio value of the higher aliphatic alcohol which is involved in the α-gel is three times the amount (in moles) of the hydrophilic anionic surfactant multiplied by the average molecular weight of the higher aliphatic alcohol. Therefore, the blend ratio of the higher aliphatic alcohol must be higher than this value and the excess amount must be 0.5-10 wt %. An amphiphilic substance other than a higher aliphatic alcohol can also be blended in. The melting point of the amphiphilic substance is preferably 55° C. or higher, more preferably 60° C. or higher. If this melting point is lower than 55° C. then the temperature stability of the system decreases and creaming may occur. Examples of preferable amphiphilic substances include glyceryl monoalkyl ether, monoglyceride, and batyl alcohol. When both the higher aliphatic alcohol and the amphiphilic substance which are not involved in the formation of the gel are blended in, the total blend ratio of the two is 0.5-1.0 wt %.

As mentioned above, the blend ratio of the extra amount of the higher aliphatic alcohol which is not involved in the formation of the gel or the amphiphilic substance other than a higher alcohol needs to be 0.5-10 wt % of the total amount of the oil-in-water emulsion composition. If this blend ratio is less than 0.5 wt %, then the amount of the crystals of the extra higher alcohol or the amphiphilic substance is small and maintaining sufficient high temperature stability may not be possible. If the blend ratio is more than 10 wt % then the hardness becomes too high, depending on the composition, and the sensation during use becomes poor. Both can be blended in together, and the total blend ratio should be 1-10 wt %.

In the present invention, in addition to the aforementioned hydrophilic anionic surfactant, which is an essential ingredient to form the gel, lipophilic non-ionic surfactants, cationic surfactants, anionic surfactants or amphiphilic surfactants can be blended in within the range that would not affect the effects of the present invention. A hydrophilic anionic surfactant which is not involved in the formation of the gel can also be present.

The blend ratio of water in the oil-in-water emulsion composition of the present invention, which is determined according to the product, is in the range of 40-95 wt % of the total amount of the oil-in-water emulsion composition.

Selection of the oil ingredient depends on the product; the blend ratio is 3-50 wt % of the total amount of the oil-in-water emulsion composition. In the present invention, the oil ingredient does not include the aforementioned higher aliphatic alcohol and the amphiphilic substance which are the essential ingredients.

3: Description Common to the Invention in Claims 1-4

Selection of the oil ingredient blended in the oil-in-water emulsion composition of the present invention is not limited in particular as long as it is an oil ingredient normally blended in an oil-in-water emulsion composition. Examples include liquid oils/fats such as linseed oil, tsubaki oil, macadamia oil, corn oil, mink oil, olive oil, avocado oil, sasanqua oil, castor oil, safflower oil, apricot kernel oil, cinnamon oil, jojoba oil, grape oil, sunflower oil, almond oil, rape seed oil, sesame oil, wheat germ oil, rice germ oil, cotton seed oil, rice bran oil, soybean oil, tea seed oil, evening primrose oil, egg yolk oil, neatsfoot tallow, liver oil, triglycerin, glyceryl trioctanoate, glyceryl triisopalmitate; liquid or solid fats/oils such as cocoyl oil, palm oil, and palm kernel oil; solid fats/oils such as cacao butter, beef tallow, sheep tallow, lard, horse oil, hardened oil, hydrogenated castor oil, Japanese core wax, and shear butter; waxes such as beeswax, candelilla wax, cotton wax, carnauba wax, bayberry wax, tree wax, whale wax, montan wax, bran wax, lanolin, reduction lanolin, hard lanolin, kapok wax, sugarcane wax, jojoba wax, and shellac wax; octanoic esters such as cetyl octanoate; isooctanoic esters such as glyceryl tri-2-ethylhexanoate and pentaerythritol tetra-2-ethylhexanoate; lauric esters such as hexyl laurate; myristic esters such as isopropyl myristate and octyldodecyl myristate; palmitic esters such as octyl palmitate; stearic esters such as isocetyl stearate; isostearic esters such as isopropyl isostearate; isopalimitic esters such as octyl isopalmitate; oleic esters such as isodecyl oleate; adipic esters such as diisopropyl adipate; cebacic diesters such as diethyl cebacate; ester oils such as diisostearyl malate; hydrocarbon oils such as liquid paraffin, ozokerite, squalane, squalene, pristane, petrolatum, isoparaffin, ceresin, petrolatum, and microcrystalline wax; chain silicones such as dimethyl polysiloxane, methylphenyl polysiloxane, and methylhydrogen polysiloxane; ring silicones such as octamethylcyclotetrasiloxane, decamethyl cyclopenta siloxane, and dodecamethyl cyclohexane siloxane; silicone resins with a three-dimensional network structure; and silicone oils such as silicone rubber.

The present invention containing the aforementioned essential ingredients forms a gel composed of hydrophilic non-ionic surfactant or hydrophilic anionic surfactant-higher aliphatic alcohol-water in a cream-like oil-in-water emulsion composition. Since the blend ratio of the hydrophilic non-ionic surfactant is 1 wt % or less, the amount of the gel formed is small and therefore the sensation during use is refreshing and light. Since an extra amount of high-melting point higher aliphatic alcohol crystals is present along with the gel, sufficient solidification is achieved and creaming can be prevented despite the fact that the amount of the gel is small. The present invention provides an oil-in-water emulsion composition with good stability over time and good usability although only a small amount of the surfactant is blended in.

The oil-in-water emulsion composition containing the aforementioned essential ingredients can be prepared by a conventional method in the form of an endermic liniment which is a cosmetic, drug, or quasi-drug. It is preferably used as an endermic liniment which in principle has the oil-in-water cream formulation wherein gel is formed in the system. Within a range which does not affect the effect of the present invention, common effective ingredients and base ingredients can be blended in.

Such effective ingredients include, if the endermic liniment of the present invention is used as a sun care product, for example, ultraviolet light absorbents. Examples include benzoic acid type ultraviolet light absorbents such as paraamino benzoic acid; anthranilic acid type ultraviolet light absorbents such as methyl anthranilate; salicylic acid type ultraviolet light absorbents such as phenyl salicylate and octyl salicylate; cinnamic acid type ultraviolet light absorbents such as isopropyl paramethoxycinnamate, octyl paramethoxycinnamate, 2-ethylhexyl paramethoxycinnamate, glyceryl mono-2-ethylhexanoate diparamethoxycinnamate, and [4-bis(trimethylsiloxy)methylsilyl-3-methylbutyl]-3,4,5-trimethoxy cinnamic ester; benzophenone type ultraviolet light absorbents such as 2,4-dihydroxybenzophenone, 2-hydroxy-4-methoxybenzophenone, 2-hydroxy-4-methoxybenzophenone-5-sulfonic acid, sodium 2-hydroxy-4-methoxybenzophenone-5-sulfonate; urocanic acid, ethyl urocanate, 2-phenyl-5-methylbenzoxazole, 2-(2-hydroxy-5-methylphenyl)benzotriazol, and 4-tert-butyl-4'-methoxy dibenzoylmethane.

For the purpose of giving a moisture retaining effect to the endermic liniment of the present invention, humectants can be blended in; examples include polyethylene glycol, propyleneglycol, di propyleneglycol, glycerin, diglycerine, 1,3-butylene glycol, hexylene glycol, xylitol, sorbitol, maltitol, maltose, D-mannitol, starch syrup, grape sugar, fruit sugar, lactose, sodium chondroitin sulfate, sodium hyaluronate, sodium adenosine phosphate, sodium lactate, bile salts, pyrrolidone carboxylic acid, glucosamine, and cyclodextrin.

For the effective ingredients, vitamins which are used for purposes other than as an oil soluble antioxidant; hormones such as estradiol and ethynylestradiol; amino acids such as arginine, aspartic acid, cystine, cysteine, methionine, serine, leucine, and tryptophan; antiinflammatory agents such as allantoin, azulene, and glycyrrhetimic acid; whitening agents such as arbutin; astringents such as zinc oxide and tannic acid; refreshing agents such as menthol and camphor; sulfur, lysozyme chloride, pyridoxine hydrochloride, γ-oryzanol, etc. can be blended in.

Also, extracts with a variety of medicinal effects can be blended in the endermic liniment of the present invention. Examples include houttuynia extract, cork tree bark extract, melilot extract, lamium album extract, glycyrrhiza extract, peony extract, *saponaria officinalis* extract, looffah extract, cinchona extract, saxifraga extract, *sophora angustifolia* extract, *nuphar japonicum* extract, anise extract, primula extract, rose extract, rehmannia root extract, lemon extract, lithospermum root extract, aloe extract, calamus extract, eucalyptus extract, *equisetum arvense* extract, sage extract, thyme extract, tea extract, seaweed extract, cucumber extract, *syzygium aromaticum*, raspberry extracts, melissa extracts, carrot extracts, marronnier extracts, peach extracts, peaches leaf extract, mulberry extracts, cornflower extract, *hamamelis* extracts, placental extract, thymus gland extract, and silk extract.

Selection of the effective ingredients of the endermic liniment of the present invention is not limited to the aforementioned effective ingredients. The aforementioned effective ingredients can be blended in the endermic liniment of the present invention independently or in combinations of two or more as necessary for a specific purpose.

For the base ingredients of the present invention, in addition to the aforementioned essential ingredients, prior art base ingredients as required for the desired form can be blended in within the range which does not affect the effect of the present invention.

For example, the following can be blended in the end ermic liniment: lower alcohols such as ethanol, propanol, and isopropanol; sterols such as cholesterol, sitosterol, phytosterol, and lanosterol; plant type polymers such as gum arabic, traganth gum, galactan, carob gum, guar gum, karaya gum, carrageenan, pectin, agar, quin seed (quince), algae colloid (brown alga extract), and starch (rice, corn, potato, wheat); microbe type polymers such as dextran, succinoglucan, and pluran; starch type polymers such as carboxymethyl starch and methylhydroxypropyl starch; animal type polymers such as collagen, casein, albumin, and gelatin; cellulose type polymers such as methyl cellulose, nitro cellulose, ethyl cellulose, methylhydroxypropypl cellulose, hydroxyethyl cellulose, sodium cellulose sulfate, hydroxypropyl cellulose, sodium carboxymethyl cellulose, crystalline cellulose, and cellulose powder; arginic acid type polymers such as sodium arginate and arginic propylene glycol ester; vinyl type polymers such as polyvinylmethyl ether and carboxyvinyl polymer; polyoxyethylene type polymers; polyoxyethylene-polyoxypropylene copolymer type polymers; acrylic polymers such as sodium polyacrylate, polyethyl acrylate, and polyacrylic acid amide; and inorganic water soluble polymers such as polyethylene imine, cation polymer, bentonite, aluminum magnesium silicate, laponite, hectorite, and silicic anhydride.

In addition, the following can be blended in the endermic liniment of the present invention within the range that does not affect the effect of the present invention: sequestering agents such as alanine, sodium edetate, sodium polyphosphate, sodium metaphosphate, and phosphoric acid; neutralizers such as 2-amino-2-methyl-1-propanol, 2-amino-2-methyl-1,3-propanediol, potassium hydroxide, sodium hydroxide, L-arginine, L-lysine, triethanolamine, and sodium carbonate; pH adjustment agents such as lactic acid, citric acid, glycolic acid, succinic acid, tartaric acid, dl-malic acid, potassium carbonate, sodium hydrogencarbonate, and ammonium hydrogencarbonate; antioxidants; antimicrobial agents such as benzoic acid, salicylic acid, carbolic acid, para oxybenzoic acid ester, para chloro metacresol, hexachlorophene, benzalkonium chloride, chloride chlorohexidine, trichlorocarbanilide, photosensitive agents, phenoxyethanol, and paraben; perfumes, and pigments.

EXAMPLES

The present invention is described in detail below by referring to Examples and Comparative examples. The technical scope of the present invention is not limited to these Examples. The blend ratios in these Examples are expressed in weight percent units of the entire system into which the ingredient is blended, unless specified otherwise.

1: The Invention of Claims 1 and 2

The oil-in-water emulsion compositions with compositions of Examples and Comparative examples shown in Table 1-1 and Table 1-2 were prepared, and used as samples for evaluating the stability over time and usability. The results are also shown in the tables. In the ingredient names in the Tables, (a) means a hydrophilic non-ionic surfactant, (b) means a higher aliphatic alcohol, and (c) means an amphiphilic substance.

[Stability Over Time]

Each sample was stored at 50° C. for a month and then visually observed for evaluation based on the following criteria:

(Evaluation)

◯: No change was observed.

Δ: A slight separation of the water phase was observed.

X: A significant separation of the water phase was observed.

[Usability]

Each sample was observed for evaluation based on the following criteria:

◯: The sensation during use was light.

Δ: The sensation during use was somewhat heavy.

X: The sensation during use was heavy.

[Preparation Method]

The water phase ingredients and the oil phase ingredients in the formula were separately mixed, and the oil phase, heated up to 70° C., was added to the water phase at 70° C. After homogeneous emulsification with a homomixer, the temperature was cooled down to room temperature to obtain a cream-like oil-in-water emulsion composition.

TABLE 1-1

| Example | Comparative example |
| --- | --- |

TABLE 1-1-continued

|  | 1-1 | 1-2 | 1-3 | 1-1 | 1-2 | 1-3 |
|---|---|---|---|---|---|---|
| (Oil phase) | | | | | | |
| POE (30) behenyl ether (a) | 0.8 | — | 1.0 | 0.8 | — | 2 |
| POE (20) behenyl ether (a) | — | 0.2 | — | — | 0.5 | — |
| Behenyl alcohol (b) | 2 | 4 | 5 | — | — | 5 |
| Stearyl alcohol (b) | 2 | 2 | — | 0.8 | 15 | 5 |
| Tetra-2-ethylhexanoic acid Pentaerythritol | 10 | 10 | 10 | 10 | 10 | 10 |
| Squalane | 5 | 5 | 5 | 5 | 5 | 5 |
| Petrolatum | 2 | 2 | 2 | 2 | 2 | 2 |
| Ethyl paraben | 0.1 | 0.1 | 0.1 | 0.1 | 0.1 | 0.1 |
| Butyl paraben | 0.1 | 0.1 | 0.1 | 0.1 | 0.1 | 0.1 |
| (Water phase) | | | | | | |
| Trisodium edetate | 0.1 | 0.1 | 0.1 | 0.1 | 0.1 | 0.1 |
| Glycerine | 5 | 5 | 5 | 5 | 5 | 5 |
| Ion exchanged water | Balance | Balance | Balance | Balance | Balance | Balance |
| Evaluation | | | | | | |
| Long term stability | ○ | ○ | ○ | X | ○ | ○ |
| Usability | ○ | ○ | ○ | Δ | X | X |
| Amount (in moles) of the higher alcohol (mol) *1 | 0.01394 | 0.02048 | 0.01645 | 0.002963 | 0.05556 | 0.03484 |
| Amount (in moles) of the surfactant (mol) *1 | 0.000486 | 0.000166 | 0.000608 | 0.000486 | 0.000415 | 0.001215 |
| Higher alcohol involved in the gel (%) | 0.42 | 0.15 | 0.55 | 0.39 | 0.34 | 1.05 |
| Higher alcohol not involved in the gel (%) | 3.58 | 5.85 | 4.45 | 0.41 | 14.66 | 8.95 |
| Transition temperature of the gel | 70° C. | 73° C. | 76° C. | 68° C. | 68° C. | 70° C. |

[Molecular weight used]

| | |
|---|---|
| POE (30) behenyl ether | 1646 |
| POE (20) behenyl ether | 1206 |
| POE (20) stearyl ether | 1150 |
| POE (15) oleyl ether | 928 |
| Behenyl alcohol | 304 |
| Stearyl alcohol | 270 |
| Cetostearyl alcohol | 259 |

*1: Moles contained in 100 g of the oil-in-water emulsion composition
Higher alcohol involved in the gel (g) = Amount (in moles) of surfactant × 3 × average molecular weight of higher alcohol
In the case of a higher alcohol with a single linear alkyl chain and a surfactant with a single linear alkyl chain. it is known that three moles of the higher alcohol and one mole of the surfactant form the gel; therefore, the amount of the higher alcohol not involved in the gel can be determined by calculations.
Higher alcohol not involved in the gel = Blend ratio of the higher alcohol − Higher alcohol involved in the gel In Table 1-1, Examples 1-1~1-3 and Comparative examples 1-1~1-3 investigate the blend ratio of the hydrophilic non-ionic surfactant and the blend ratio of the higher aliphatic alcohol. Examples 1-1~1-3, for which the blend ratios of the hydrophilic non-ionic surfactant and the higher aliphatic alcohol are both adequate, show good long-term stability and usability. Comparative example 1-1, for which the blend ratio of the extra higher aliphatic alcohol which is not involved in the gel formation is less than 1 wt %, shows inferior long-term stability. Comparative example 1-2, for which the blend ratio is over 10 wt %, shows inferior usability. Comparative example 1-3, for which the blend ratio of the surfactant is 2 wt %, shows inferior usability.

TABLE 1-2

| | Example | | | Comparative example | |
|---|---|---|---|---|---|
| | 1-4 | 1-5 | 1-6 | 1-4 | 1-5 |
| (Oil phase) | | | | | |
| POE (30) behenyl ether (a) | 0.5 | — | — | 0.1 | — |
| POE (20) beheny ether (a) | — | 0.8 | 0.8 | — | — |
| POE (15) oleyl ether (a) | — | — | — | — | 0.7 |
| Behenyl alcohol (b) | 3 | 2 | 2 | 4 | — |
| Stearyl alcohol (b) | 2 | 2 | — | — | — |
| Cetostearyl alcohol (b) | — | — | — | — | 4 |
| Batyl alcohol (c) | — | — | 2 | — | — |
| Pentaerythritol tetra-2-ethylhexanoate | 10 | — | — | 10 | — |

TABLE 1-2-continued

|  | Example | | | Comparative example | |
|---|---|---|---|---|---|
|  | 1-4 | 1-5 | 1-6 | 1-4 | 1-5 |
| Di-2-ethylhexyl succinate | — | 5 | 5 | — | 5 |
| Squalane | 5 | — | — | 5 | — |
| Liquid petrolatum | — | 10 | 10 | — | 10 |
| Petrolatum | 2 | 2 | 2 | 2 | 2 |
| Ethyl paraben | 0.1 | 0.1 | 0.1 | 0.1 | 0.1 |
| Butyl paraben | 0.1 | 0.1 | 0.1 | 0.1 | 0.1 |
| (Water phase) | | | | | |
| Trisodium edetate | 0.1 | 0.1 | 0.1 | 0.1 | 0.1 |
| Glycerine | 5 | 5 | 5 | 5 | 5 |
| Ion exchanged water | Balance | Balance | Balance | Balance | Balance |
| Evaluation | | | | | |
| Long-term stability | ○ | ○ | ○ | X | X |
| Usability | ○ | ○ | ○ | ○ | ○ |
| Amount (in moles) of the higher alcohol (mol) *1 | 0.01724 | 0.01394 | 0.006579 | 0.01316 | 0.01544 |
| Amount (in moles) of the surfactant (mol) *1 | 0.00304 | 0.000696 | 0.000696 | 0.000061 | 0.000754 |
| Higher alcohol involved in the gel (%) | 0.26 | 0.60 | 0.63 | 0.06 | 0.59 |
| Higher alcohol not involved in the α gel (%) | 4.74 | 3.40 | 3.37 | 3.95 | 3.41 |
| Transition temperature of the gel | 72° C. | 68° C. | 70° C. | 70° C. | 53° C. |

*1: Moles contained in 100 g of the oil-in-water emulsion composition

In Table 1-2, Examples 1-4~1-6 show good long-term stability and usability, which is the effect pertaining to the present invention. Comparative example 1-4 has a blend ratio of the hydrophilic non-ionic surfactant of 0.1%, which is outside of the standard range, and shows inferior long-term stability. In Comparative example 1-5, the formula of the higher aliphatic alcohol-hydrophilic non-ionic surfactant-water system is set such that the gel transition temperature would be less than 60° C. This Comparative example 1-5 shows inferior long-term stability.

2: The Invention of Claims 3 and 4

The oil-in-water emulsion compositions with compositions of Examples and Comparative examples shown in Table 2-1 and Table 2-2 were prepared, and used as samples for evaluating the stability over time and usability. The results are also shown in the tables. In the ingredient names in the Tables, (a) means a hydrophilic anionic surfactant, (b) means a higher aliphatic alcohol, and (c) means an amphiphilic substance.

[Stability Over Time]

Each sample was stored at 50° C. for a month and then visually observed for evaluation based on the following criteria:
(Evaluation)
○: No change was observed.
Δ: A slight separation of the water phase was observed.
X: A significant separation of the water phase was observed.
[Usability]
Each sample was observed for evaluation based on the following criteria:
○: The sensation during use was light.
Δ: The sensation during use was somewhat heavy.
X: The sensation during use was heavy.
[Preparation Method]

The water phase ingredients and the oil phase ingredients in the formula were separately mixed, and the oil phase, heated up to 70° C., was added to the water phase at 70° C. After homogeneous emulsification with a homomixer, the temperature was cooled down to room temperature to obtain a cream-like oil-in-water emulsion composition.

TABLE 2-1

|  |  | Example 2-1 | Example 2-2 | Example 2-3 | Example 2-4 | Example 2-5 | Example 2-6 | Comparative example 2-1 | Comparative example 2-2 | Comparative example 2-3 | Comparative example 2-4 |
|---|---|---|---|---|---|---|---|---|---|---|---|
| Oil phase | Behenyl alcohol (b) | 1 | 1 | 1 | 2 | 1 | 2 | 1 | 5 | 1.5 | 2.5 |
|  | Stearyl alcohol (b) |  | 0.2 | 1 | 2 | 1 | 2.5 |  | 8 | 1 | 2 |
|  | Pentaerythritol tetra-2-ethylhexanoate | 1 | 1 | 1 | 1 | 1 | 1 | 1 | 1 | 1 | 1 |
|  | Squalane | 3 | 3 | 3 | 3 | 3 | 3 | 3 | 3 | 3 | 3 |
|  | Petrolatum | 1 | 1 | 1 | 1 | 1 | 1 | 1 | 1 | 1 | 1 |
| Water phase | Monosodium N-stearoyl-L-glutamate (a) | 0.1 | 0.25 | 0.4 | 0.4 |  |  | 0.05 | 0.4 | 1.2 |  |
|  | Sodium cetylphosphate (a) |  |  |  |  | 0.2 | 0.4 |  |  |  | 1.5 |

TABLE 2-1-continued

| | | | | | | | | | | |
|---|---|---|---|---|---|---|---|---|---|---|
| Glycerine | 5 | 5 | 4 | 4 | 4 | 4 | 5 | 5 | 5 | 5 |
| Dipropylene glycol | 5 | 5 | 5 | 5 | 5 | 4 | 5 | 5 | 5 | 5 |
| Trisodium edetate | 0.1 | 0.1 | 0.1 | 0.1 | 0.1 | 0.1 | 0.1 | 0.1 | 0.1 | 0.1 |
| Methyl paraben | 0.15 | 0.15 | 0.15 | 0.15 | 0.15 | 0.15 | 0.15 | 0.15 | 0.15 | 0.15 |
| Ion exchanged water | Balance | Balance | Balance | Balance | Balance | Balance | Balance | Balance | Balance | Balance |
| Long term stability | ○ | ○ | ○ | ○ | ○ | ○ | X | ○ | ○ | ○ |
| Usability | ○ | ○ | ○ | Δ | ○ | ○ | Δ | X | X | X |
| Amount (in moles) of the higher alcohol (mol) *1 | 0.003289 | 0.004022 | 0.006969 | 0.013937 | 0.006969 | 0.015783 | 0.003289 | 0.045924 | 0.008609 | 0.015577 |
| Amount (in moles) of the surfactant (mol) *1 | 0.000227 | 0.000568 | 0.000909 | 0.000909 | 0.000608 | 0.001216 | 0.000114 | 0.000909 | 0.002727 | 0.004559 |
| Higher alcohol involved in the gel (%) | 0.21 | 0.51 | 0.78 | 0.78 | 0.52 | 1.04 | 0.10 | 0.77 | 2.38 | 3.95 |
| Higher alcohol not involved in the gel (%) | 0.79 | 0.69 | 1.22 | 3.22 | 1.48 | 3.46 | 0.90 | 12.23 | 0.12 | 0.55 |
| Transition temperature of the gel | 78° C. | 75° C. | 74° C. | 74° C. | 74° C. | 75° C. | 75° C. | 75° C. | 75° C. | 76° C. |

[Molecular weight used]

| | |
|---|---|
| Monosodium N-stearoyl-L-glutamate | 440 |
| Sodium cetylphosphate | 329 |
| Behenyl alcohol | 304 |
| Stearyl alcohol | 270 |

*1: Moles contained in 100 g of the oil-in-water emulsion composition

Higher alcohol involved in the gel = Amount (in moles) of surfactant × 3 × average molecular weight of higher alcohol In the case of a higher alcohol with a single linear alkyl chain and a surfactant with a single linear alkyl chain, it is known that three moles of the higher alcohol and one mole of the surfactant form the gel; therefore, the amount of the higher alcohol not involved in the gel can be determined by calculations.

Higher alcohol not involved in the gel (%) = Blend ratio of the higher alcohol − Higher alcohol involved in the gel In Table 2-1, Examples 2-1~2-6 and Comparative examples 2-1~2-4 investigate the blend ratio of the hydrophilic anionic surfactant and the blend ratio of the higher aliphatic alcohol. Examples 2-1~2-6, for which the blend ratios of the hydrophilic anionic surfactant and the higher aliphatic alcohol are both adequate, show good long-term stability and usability. Comparative example 2-1, for which the blend ratio of the hydrophilic anionic surfactant is less than 0.1 wt %, and Comparative example 2-3, for which the blend ratio of the extra higher aliphatic alcohol which is not involved in the gel formation is less than 0.5 wt %, show inferior long-term stability. Comparative example 2-2, for which the blend ratio of the extra higher aliphatic alcohol which is not involved in the gel formation is over 10 wt %, and Comparative example 2-4, for which the blend ratio of the surfactant is 1.5 wt %, shows inferior usability.

TABLE 2-2

| | Example 2-7 | Example 2-8 | Example 2-9 | Comparative example 2-5 | Comparative example 2-6 |
|---|---|---|---|---|---|
| Behenyl alcohol (b) | 1 | 1 | 3 | 1 | |
| Stearyl alcohol (b) | 0.2 | 0.2 | 3 | 0.2 | |
| Cetyl alcohol (b) | | | | | 1.2 |
| Batyl alcohol (c) | | 1 | | | |
| Pentaerythritol tetra-2-ethylhexanoate | 2 | 2 | 5 | 1 | 1 |
| Squalane | 3 | 2 | 5 | 3 | 3 |
| Petrolatum | 1 | 1 | 3 | 1 | 1 |
| Dimethyl silicone (6cs) | 3 | 1 | 5 | 0.5 | 0.5 |
| Monosodium N-stearoyl-L-glutamate (a) | 0.2 | 0.4 | | 0.07 | 0.2 |
| Sodium cetylphosphate (a) | | | 0.3 | | |
| Glycerine | 5 | 5 | 5 | 5 | 5 |
| Dipropylene glycol | 5 | 5 | 5 | 5 | 5 |
| Trisodium edetate | 0.1 | 0.1 | 0.1 | 0.1 | 0.1 |
| Methyl paraben | 0.15 | 0.15 | 0.15 | 0.15 | 0.15 |
| Ion exchanged water | Balance | Balance | Balance | Balance | Balance |
| Long-term stability | ○ | ○ | ○ | X | X |
| Usability | ○ | ○ | ○ | ○ | ○ |
| Amount (in moles) of the higher alcohol (mol) *1 | 0.00402 | 0.00402 | 0.02091 | 0.00402 | 0.00469 |
| Amount (in moles) of the surfactant (mol) *1 | 0.00045 | 0.00091 | 0.00091 | 0.00016 | 0.00045 |

TABLE 2-2-continued

|  | Example 2-7 | Example 2-8 | Example 2-9 | Comparative example 2-5 | Comparative example 2-6 |
|---|---|---|---|---|---|
| Higher alcohol involved in the gel (%) | 0.41 | 0.81 | 0.79 | 0.14 | 0.35 |
| Higher alcohol or amphiphilic substance not involved in the gel (%) | 0.79 | 1.39 | 5.21 | 1.06 | 0.85 |
| Transition temperature of the gel | 75° C. | 75° C. | 73° C. | 75° C. | 58° C. |

*1: Moles contained in 100 g of the oil-in-water emulsion composition

In Table 2-2, Examples 2-7~2-9 show good long-term stability and usability, which is the effect pertaining to the present invention. Comparative example 2-5 has a blend ratio of the hydrophilic anionic surfactant of 0.1 wt %, which is outside of the standard range, and shows inferior long-term stability. In Comparative example 2-6, the formula of the higher aliphatic alcohol-hydrophilic anionic surfactant-water system is set such that the gel transition temperature would be less than 60° C. This Comparative example 2-6 shows inferior long-term stability.

Industrial Applicability of the Invention

The present invention is an oil-in-water emulsion composition containing a hydrophilic non-ionic surfactant or hydrophilic anionic surfactant, a higher aliphatic alcohol, water, and an oil ingredient which meets specific conditions. This is an oil-in-water emulsion composition with good high temperature stability and usability, and can be used as a cream-like endermic liniment such as a cosmetic.

The invention claim is:

1. An oil-in-water emulsion cream comprising:
   (a) between 0.3 and 0.8 wt % of a hydrophilic non-ionic surfactant,
   (b) water,
   (c) an oil ingredient,
   (d) a first higher aliphatic alcohol; and
   (e) a second higher aliphatic alcohol and/or amphiphilic substance, neither of which is involved in the formation of the α-gel,
   wherein the hydrophilic non-ionic surfactant, water and a first higher aliphatic alcohol, form an α-gel having a transition temperature of 60° C. or higher; the blend ratio of the hydrophilic non-ionic surfactant which forms said α-gel is between 0.3 and 0.8 wt % of the total amount of the oil-in-water emulsion composition; the molar blend ratio of the hydrophilic non-ionic surfactant and first higher aliphatic alcohol which form the α-gel is 1:3; the blend ratio of the second higher aliphatic alcohol and/or amphiphilic substance which are not involved in the formation of the α-gel is 1-10 wt % of the total amount of the oil-in-water emulsion, and the second higher aliphatic alcohol is the same as or different than the first aliphatic alcohol.

2. The oil-in-water emulsion cream of claim 1, wherein said oil-in-water emulsion composition is a cream-like endermic liniment.

3. The oil-in-water emulsion cream of claim 1, wherein the first higher aliphatic alcohol is a mixture of two or more higher aliphatic alcohols.

4. The oil-in-water emulsion cream of claim 1, wherein the first higher aliphatic alcohol is a combination of two or more different higher aliphatic alcohols for which the melting point of the mixture is 60° C. or higher.

5. The oil-in-water emulsion cream of claim 4, wherein the first higher aliphatic alcohol is a mixture of stearyl and behenyl alcohol.

6. The oil-in-water emulsion cream of claim, wherein said α-gel has a transition temperature of 65° C. or higher.

7. The oil-in-water emulsion cream of claim 1, wherein the second higher aliphatic alcohol is a combination of two or more different higher aliphatic alcohols for which the melting point of the mixture is 60° C. or higher.

8. The oil-in-water emulsion cream of claim 1, wherein the melting point of said amphiphilic substance is 55° C. or higher.

9. The oil-in-water emulsion cream of claim 1, wherein the total blend ratio of the second higher aliphatic alcohol and the amphiphilic substance is 0.1-1.0 wt %.

10. The oil-in-water emulsion cream of claim 1, wherein the oil ingredient, which does not include the second higher aliphatic alcohol or amphiphilic substance, constitutes from 5-50 wt % of the total amount of the oil-in-water composition.

11. The oil-in-water emulsion cream of claim 1, wherein the oil ingredient, which does not include the second higher aliphatic alcohol and/or amphiphilic substance, constitutes from 3-50 wt % of the total amount of the oil-in-water composition.

* * * * *